(12) United States Patent
Wilson et al.

(10) Patent No.: US 8,409,139 B2
(45) Date of Patent: *Apr. 2, 2013

(54) STRETCH RESISTANT THERAPEUTIC DEVICE

(75) Inventors: Peter Wilson, Foster City, CA (US); Eric Leopold, Redwood City, CA (US); Rupesh K. Desai, San Jose, CA (US)

(73) Assignee: Micrus Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,789

(22) Filed: Apr. 10, 2012

(65) Prior Publication Data

US 2012/0197288 A1    Aug. 2, 2012

Related U.S. Application Data

(60) Continuation of application No. 12/032,140, filed on Feb. 15, 2008, now Pat. No. 8,167,838, which is a division of application No. 11/435,304, filed on May 16, 2006, now Pat. No. 7,572,246, which is a continuation of application No. 10/202,459, filed on Jul. 23, 2002, now Pat. No. 7,608,058.

(51) Int. Cl.
 *A61F 7/12* (2006.01)
(52) U.S. Cl. ........................ 604/113; 606/200
(58) Field of Classification Search .................. 606/200; 604/113

See application file for complete search history.

(56) References Cited

U.S. PATENT DOCUMENTS

| | | | |
|---|---|---|---|
| 3,452,742 A | 7/1969 | Muller | |
| 3,485,234 A | 12/1969 | Stevens | |
| 4,998,916 A | 3/1991 | Hammerslag et al. | |
| 5,203,772 A | 4/1993 | Hammerslag et al. | |
| 5,226,911 A | 7/1993 | Chee et al. | |
| 5,354,295 A | 10/1994 | Guglielmi et al. | |
| 5,522,819 A | 6/1996 | Graves et al. | |
| 5,582,619 A | 12/1996 | Ken | |
| 5,833,705 A | 11/1998 | Ken et al. | |
| 5,853,418 A | 12/1998 | Ken et al. | |
| 5,976,162 A | 11/1999 | Doan et al. | |
| 6,004,338 A | 12/1999 | Ken et al. | |
| 6,013,084 A | 1/2000 | Ken et al. | |
| 6,102,932 A * | 8/2000 | Kurz | 606/200 |
| 6,165,178 A | 12/2000 | Bashiri et al. | |
| 6,193,623 B1 | 2/2001 | Koch et al. | |
| 6,193,728 B1 | 2/2001 | Ken et al. | |
| 6,211,964 B1 | 4/2001 | Luscombe et al. | |
| 6,296,622 B1 | 10/2001 | Kurz et al. | |
| 6,478,773 B1 * | 11/2002 | Gandhi et al. | 604/113 |
| 6,679,903 B2 | 1/2004 | Kurz | |
| 7,166,122 B2 | 1/2007 | Aganon et al. | |
| 7,422,569 B2 | 9/2008 | Wilson et al. | |

FOREIGN PATENT DOCUMENTS

| | | |
|---|---|---|
| CN | 100411593 | 9/2005 |
| DE | 19704269 | 11/1997 |
| EP | 752235 | 1/1997 |
| EP | 792623 | 9/1997 |
| JP | 11290330 A | 10/1999 |

(Continued)

OTHER PUBLICATIONS

International Search Report, Oct. 24, 2003, 6 pages.

(Continued)

*Primary Examiner* — Vy Q Bui
(74) *Attorney, Agent, or Firm* — Fulwider Patton LLP

(57) ABSTRACT

A vasoocclusive coil is reinforced with a stretch resistant member to improve safety during retraction of the coil. The stretch resistant member is fixedly attached at one end to the vasoocclusive coil, and the other end of the stretch resistant member is detachably mounted to an elongated pusher member to allow for placement and release of the vasoocclusive coil within the patient's vasculature.

12 Claims, 4 Drawing Sheets

FOREIGN PATENT DOCUMENTS

| | | |
|---|---|---|
| JP | 2000107191 A | 4/2000 |
| JP | 2004215797 A | 8/2004 |
| JP | 2005530593 A | 10/2005 |
| WO | 92/21400 | 12/1992 |
| WO | 94/09705 | 5/1994 |
| WO | 94/10936 | 5/1994 |
| WO | 98/58590 | 12/1998 |
| WO | 99/29260 | 6/1999 |
| WO | 01/58366 | 8/2001 |

OTHER PUBLICATIONS

Japanese Office Action, Nov. 13, 2012, 3 pages.

* cited by examiner

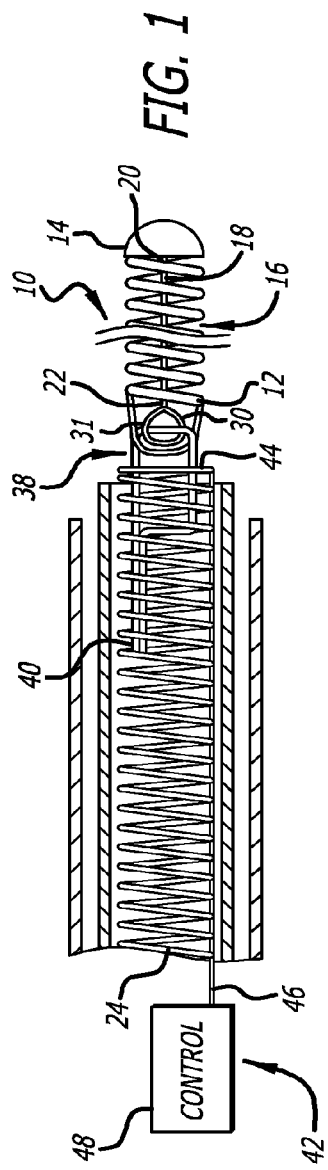
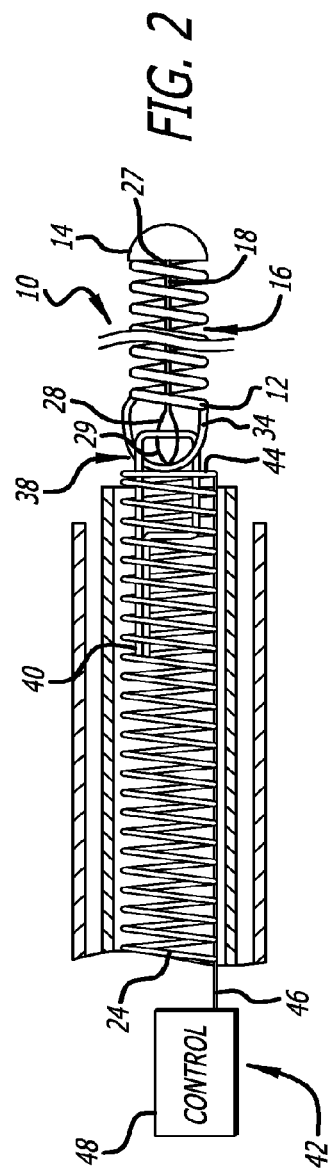
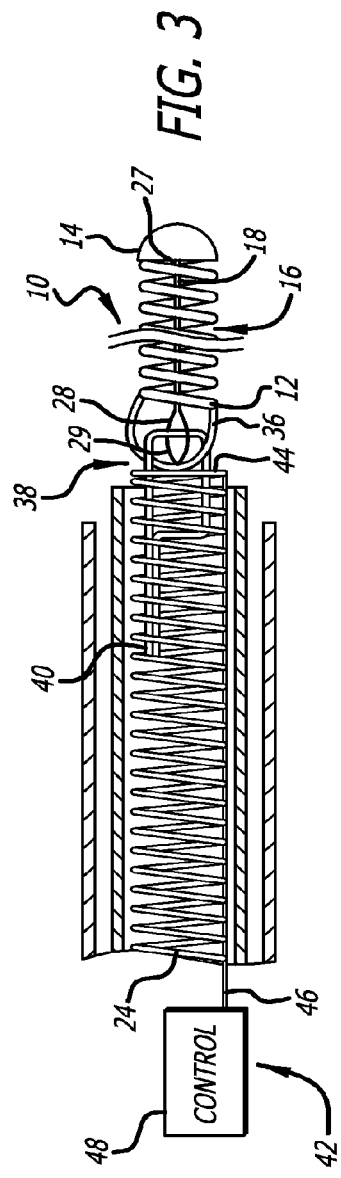

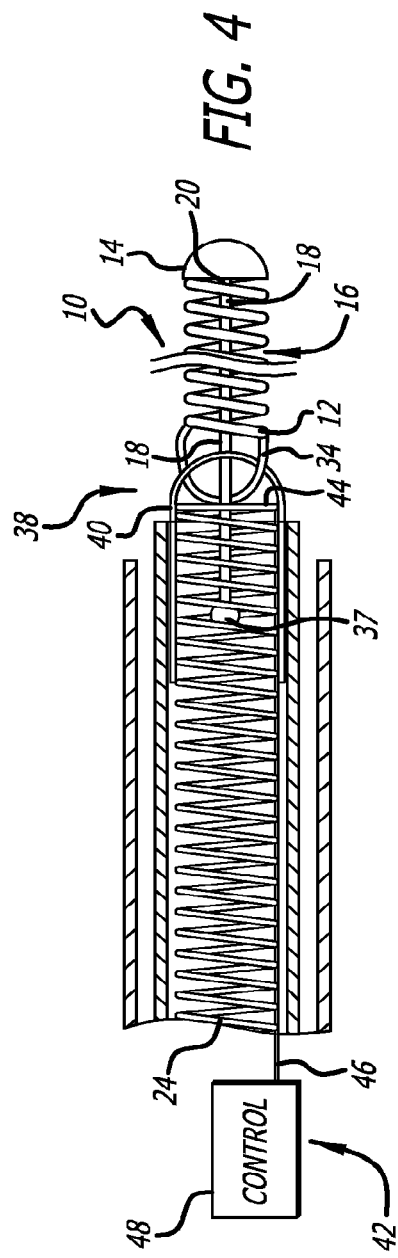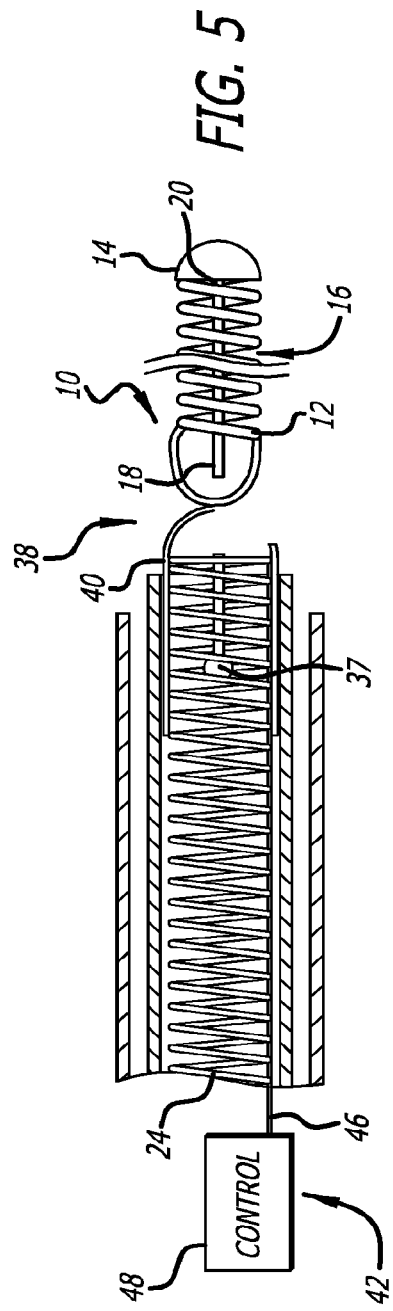

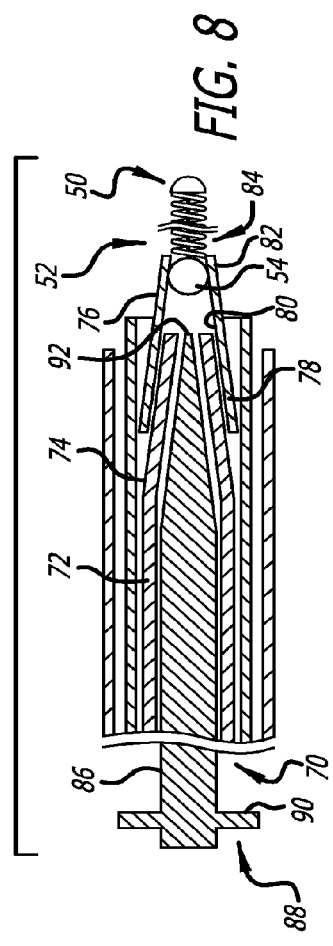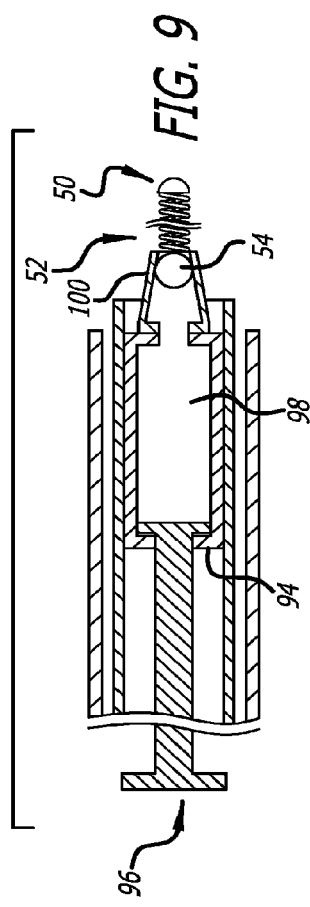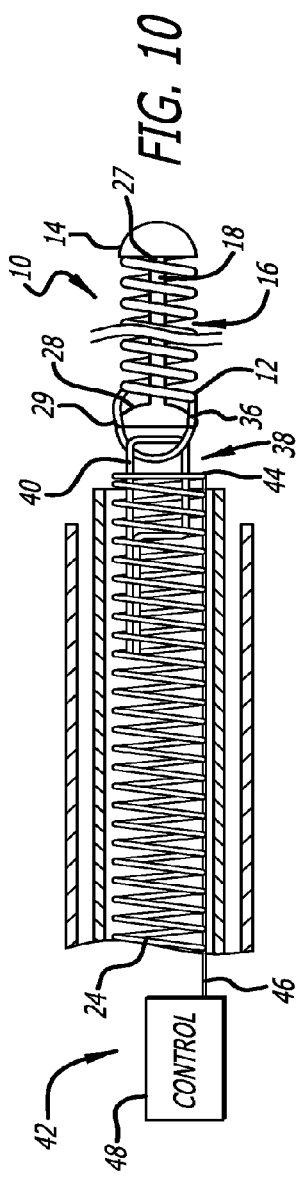

STRETCH RESISTANT THERAPEUTIC DEVICE

CROSS-REFERENCES TO RELATED APPLICATIONS

This application is a continuation of U.S. application Ser. No. 12/032,140, filed Feb. 15, 2008, now U.S. Pat. No. 8,167,838, which is a divisional of U.S. application Ser. No. 11/435,304, filed May 16, 2006, now U.S. Pat. No. 7,572,246, which is a continuation of U.S. application Ser. No. 10/202,459, filed Jul. 23, 2002, now U.S. Pat. No. 7,608,058, incorporated by reference in their entirety.

BACKGROUND

This invention relates generally to implantable devices for interventional therapeutic treatment or vascular surgery, and more particularly concerns a stretch resistant therapeutic device such as an embolic or vasoocclusive coil and an apparatus for release and deployment of the stretch resistant therapeutic device within a patient's vasculature.

The art and science of interventional therapy and surgery has continually progressed towards treatment of internal defects and diseases by use of ever smaller incisions or access through the vasculature or body openings, in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like, and the use of vasoocclusive devices to treat defects in the vasculature.

One specific field of interventional therapy that has been able to advantageously use recent developments in technology is the treatment of neurovascular defects. As smaller and more capable structures and materials have been developed, treatment of vascular defects in the human brain which were previously untreatable or represented unacceptable risks via conventional surgery have become amenable to treatment. One type of non-surgical therapy that has become advantageous for the treatment of defects in the neurovasculature has been the placement by way of a catheter of vasoocclusive devices such as embolic coils in a damaged portion of a vein or artery.

Vasoocclusive devices are therapeutic devices that are placed within the vasculature of the human body, typically via a catheter, to form an embolus to block the flow of blood through a vessel making up that portion of the vasculature, or within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645,558, which is specifically incorporated by reference herein. That vasoocclusive device comprises one or more vasoocclusive members wound to form a generally spherical or ovoid shape in a relaxed state. The vasoocclusive members can be a helically wound coil or a co-woven braid formed of a biocompatible material, and the device is sized and shaped to fit within a vascular cavity or vesicle, such as for treatment of an aneurysm or fistula. The vasoocclusive member can be first helically wound or braided in a generally linear fashion, and is then wound around an appropriately shaped mandrel or form, and heat treated to retain the shape after removal from the heating form. Radiopacity can be provided in the vasoocclusive members by weaving in synthetic or natural fibers filled with powdered radiopaque material, such as powdered tantalum, powdered tungsten, powdered bismuth oxide or powdered barium sulfate.

The delivery of such vasoocclusive devices can be accomplished by a variety of means, including via a catheter through which the device is pushed by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

Vasoocclusive coils made of platinum, gold, and other ductile materials will easily deform from their coil shape under tension, causing a potentially dangerous situation when the coil is partially in an aneurysm and partially stretched in the delivery catheter. If it is determined that the coil is improperly placed, or is too large, the coil will need to be moved or replaced. However, at this stage of the procedure, the coil can no longer be pushed, and must be slowly retracted out of the catheter as a wire. If during this procedure the coil breaks, an additional procedure must be performed to remove the coil extending out of the aneurysm. It would be desirable to reinforce such vasoocclusive coils to provide stretch resistance to the coils to reduce the risk of the coils breaking, particularly during withdrawal of a coil for relocation or replacement, in order to provide a safety factor during retraction of soft or otherwise easily stretchable coils. It would also be desirable to minimize the increase of stiffness caused by reinforcement of the coils after the coils are released in deployment of the coils in an aneurysm so that the coils can freely transform to a desired secondary shape and conform to the dimensions of the location being treated. The present invention meets these and other needs.

SUMMARY OF THE INVENTION

Briefly, and in general terms, the present invention provides for a stretch resistant therapeutic device for release and deployment within a patient's vasculature, and an apparatus for release and deployment of the stretch resistant therapeutic device within a patient's vasculature, in which the therapeutic device is a vasoocclusive coil reinforced with an inner stretch resistant member to provide stretch resistance to the coil. The incorporation of an inner stretch resistant member may also allow the coil to be pushed even when such a coil is partially deployed, to improve safety during retraction of the coil. The vasoocclusive coil may be coated with one or more therapeutic agents, which may include a hydrogel. The vasoocclusive coil is reinforced by an inner stretch resistant member that is fixedly attached at one end at or near a distal end of the vasoocclusive coil, and that is detachably mounted at the other end of the vasoocclusive coil to an elongated pusher member to allow for placement and release of the vasoocclusive coil within the patient's vasculature.

Attachment of the inner stretch resistant member toward or at the distal end of the vasoocclusive coil without connection of the inner stretch resistant member to the other end of the vasoocclusive coil minimizes the increase of stiffness caused by reinforcement of the coil after the coil is released for deployment. An additional advantage is that the coil is free floating on the proximal end over the inner stretch resistant member. The inner stretch resistant member can be used to enhance radiopacity, aid in secondary shape configurations, and can be configured to aid desired stiffness of the coil, and can allow a softer coil to be used without stretching of the coil.

The present invention accordingly provides for a stretch resistant therapeutic device for release and deployment within a patient's vasculature. The therapeutic device includes a vasoocclusive coil defining a lumen between proximal and distal ends of the coil, and a stretch resistant member extending through the lumen of the vasoocclusive coil. The stretch resistant member is fixedly attached at a first end toward a distal end of the vasoocclusive coil, and is detachably mountable at a second end to an elongated pusher member to allow for placement of the vasoocclusive coil within the patient's vasculature. The stretch resistant member may be formed as a ribbon, wire, braid, primary wind, or stranded material, and may be formed from fiber, plastic or other polymer such as an ethylene-octene copolymer, polypropylene, or polyethylene, or a metal or metal alloy, such as a nickel-titanium alloy, for example, or a metal which is radiopaque, such as platinum, for example. When the stretch resistant member is formed from a fiber such as an ethylene-octene copolymer, polypropylene, or polyethylene, a portion of the coil at or near the distal end of the coil may be attached to one end of the stretch resistant member by an adhesive or by heating of the end of the fiber. In another aspect, when the stretch resistant member is formed of a polymer such as an ethylene-octene copolymer, polypropylene, or polyethylene, the stretch resistant member may also be severable by application of heat energy to the stretch resistant member.

The present invention also provides for an apparatus for release and deployment of the stretch resistant therapeutic device within a patient's vasculature. The therapeutic device includes a vasoocclusive coil defining a lumen between proximal and distal ends of the therapeutic device. The therapeutic device may be detachably mounted to the distal end of the pusher member, for example, by at least one loop of fiber material, by a displaced coil at the proximal end of the vasoocclusive coil, or by a loop attached at the proximal end of the therapeutic device as a socket. The therapeutic device may by deployed mechanically or by injection.

In another aspect, the stretch resistant member is detachably mounted to the distal end of the elongated pusher member, and means are provided for detaching the stretch resistant member from the distal end of the elongated pusher member. In one option, a connector fiber attached to the pusher member detachably mounts the therapeutic device to the pusher member for placement of the therapeutic device within the vasculature, and means are provided for severing the connector fiber to cause the connector fiber to release the therapeutic device for deploying the therapeutic device from the pusher member when a desired placement of the therapeutic device within the vasculature is achieved. The means for severing the connector fiber may include an electrical resistance heater wire or coil, when the connector fiber is formed from a thermoplastic material, such as polyethylene, for example. When the stretch resistant member is formed of a polymer such as an ethylene-octene copolymer, polypropylene, or polyethylene, the stretch resistant member can also be severed by the means for severing in the same manner.

In another option, the proximal end of the therapeutic device includes a distal therapeutic portion and a proximal stem portion, and the proximal stem portion includes at least one rounded member. A body of constraining material is mounted to the distal end of the elongated pusher member, with the body of constraining material having a stressed configuration engaging the at least one rounded member of the stem proximal portion of the therapeutic device and a recovered configuration withdrawn from the at least one rounded member of the proximal stem portion of the therapeutic device. In one option, the body of constraining material may have a tubular cross-section forming a tubular collar extending from its proximal end to its distal end. The body of constraining material may be formed of a polymer such as polyurethane, or a nickel titanium alloy, for example.

These and other aspects and advantages of the invention will become apparent from the following detailed description and the accompanying drawings, which illustrate by way of example the features of the invention.

BRIEF DESCRIPTION OF THE DRAWINGS

FIG. 1 is a sectional view of a stretch resistant therapeutic device and an apparatus for release and deployment of the stretch resistant therapeutic device within a patient's vasculature according to the invention.

FIG. 2 is a sectional view of a first alternate embodiment of a stretch resistant therapeutic device and an apparatus for release and deployment of the stretch resistant therapeutic device within a patient's vasculature according to the invention.

FIG. 3 is a sectional view of a second alternate embodiment of a stretch resistant therapeutic device and an apparatus for release and deployment of the stretch resistant therapeutic device within a patient's vasculature according to the invention.

FIGS. 4 and 5 are sectional views illustrating a third alternate embodiment of a stretch resistant therapeutic device and apparatus for release and deployment of the stretch resistant therapeutic device within a patient's vasculature according to the invention, and illustrating release of the stretch resistant therapeutic device.

FIG. 8 is a sectional view of a fifth alternate embodiment of a stretch resistant therapeutic device and an apparatus for release and deployment of the stretch resistant therapeutic device within a patient's vasculature according to the invention.

FIG. 9 is a sectional view of a sixth alternate embodiment of a stretch resistant therapeutic device and an apparatus for release and deployment of the stretch resistant therapeutic device within a patient's vasculature according to the invention.

FIG. 10 is a sectional view of a seventh alternate embodiment of a stretch resistant therapeutic device and an apparatus for release and deployment of the stretch resistant therapeutic device within a patient's vasculature according to the invention.

DETAILED DESCRIPTION OF THE PREFERRED EMBODIMENTS

Figure 6:
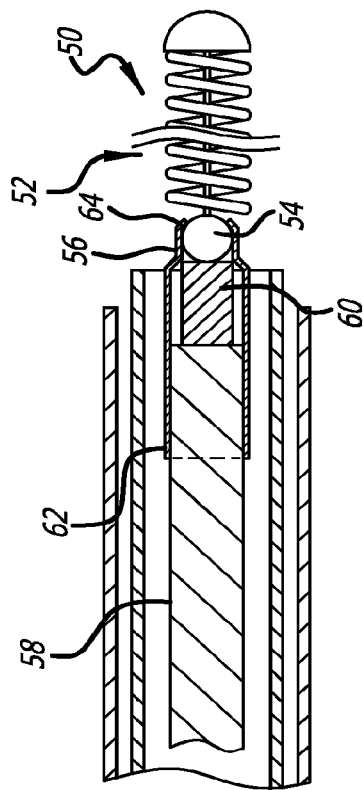
FIG. 6 is a sectional view of a fourth alternate embodiment of a stretch resistant therapeutic device and an apparatus for release and deployment of the stretch resistant therapeutic device within a patient's vasculature according to the invention.

While the deployment of therapeutic devices has typically been accomplished by using a pusher member to push such a coil through a catheter, and a variety of detachment mechanisms to release the device from a pusher have been used, such coils are typically made of ductile materials that easily deform from their coil shape once released or partially released from the delivery catheter, so that the coils can no longer be pushed, and withdrawing of the coils back through the catheter can result in breakage of the coils. The present invention provides stretch resistance to such therapeutic devices to reduce the risk of the coils breaking during withdrawal of a coil for relocation or replacement. The present invention also minimizes the increase of stiffness caused by reinforcement of the coils when the coils are deployed so that the coils can freely transform to a desired secondary shape and conform to the dimensions of the target area.

As is illustrated in the drawings, the invention is embodied in a stretch resistant therapeutic device such as a vasoocclusive or embolic coil 10 for release and deployment within a patient's vasculature. The vasoocclusive coil has a proximal end 12 and a distal end 14, and a lumen 16 extending between the proximal and distal ends. The vasoocclusive coil may be formed from a variety of materials including, but not limited to, one or more strands of a metal or metal alloy such as stainless steel or a nickel-titanium alloy, which may include a radiopaque strand, made of platinum, tungsten or gold, in order to serve as a marker, polymeric material such as a shape memory polymer, for example, and coils coated with one or more therapeutic agents, such as one or more human growth modulating factors such as interleukins, transformation growth factor b, congeners of platelet derived growth factor, and monoclonal antibodies directed against growth factors, drugs, drug producing cells, cell regeneration factors, progenitor cells of the same type as those from the aneurysm, and progenitor cells that are histologically different from those of the aneurysm, to accelerate the healing process. The coil may also be coated with a hydrogel, such as one or more hydrogels selected from organic gels and inorganic gels, and which may be combined with one or more of the therapeutic agents described above. Organic gels from which the hydrogel can be selected include, by way of example and not by way of limitation, gels formed from polysaccharides and mucopolysaccharides including, but not limited to hyaluronic acid, dextran, heparin sulfate, chondroitin sulfate, heparin, agar, starch, and alginate; polyaminoacids; proteins that support cell growth and healing, including but not limited to fibronectin, gelatin, collagen, fibrin, pectins, albumin, ovalbumin, and polyamino acids; collagen-hydroxyethyl-methacrylate (HEMA); polyphosphazines; polyphosphoesters; polyethylene glycol; polyethylene oxide; polyvinyl alcohol; polyvinylpyrrolidone; polyethyloxazoline; polyethylene oxide-co-polypropyleneoxide block copolymers; PGA-PEG-PGA block copolymers; PGA-PEG diblock copolymers; acrylates, including but not limited to diacrylates, oligoacrylates, methacrylates, dimethacrylates and oligomethoacrylates; PEG-oligoglycolylacrylates, such as described in U.S. Pat. No. 5,626,863, which is incorporated by reference herein; carboxy alkyl celluloses, including but not limited to carboxymethyl cellulose; partially oxidized cellulose; biodegradable polymers including but not limited to polymers and oligomers of glycolide, lactide, polylactic acid, polyesters of a-hydroxy acids, including lactic acid and glycolic acid, such as the poly(a-hydroxy) acids including polyglycolic acid, poly-DL-lactic, poly-L-lactic acid, and terpolymers of DL-lactide and glycolide; e-caprolactone and e-caprolactone copolymerized with polyesters; polylactones and polycaprolactones including poly(e-caprolactone), poly(d-valerolactone) and poly(gamma-butyrolactone); polyanhydrides; polyorthoesters; other hydroxy acids; polydioxanone; and other biologically degradable polymers that are non-toxic or are present as metabolites in the body; as well as non-degradable polymers such as styrene and acrolein.

Collagen-hydroxyethyl-methacrylate (HEMA) hydrogel polymer is commonly formed from a gelled and crosslinked hydrophilic monomer solution to form a three dimensional polymeric meshwork anchoring macromolecules. Crosslinking of the hydrophilic monomer solution can be accomplished by free radical polymerization of hydrophilic monomers, such as hydroxyethyl-methacrylate (HEMA). Hydrogel polymers formed by free radical polymerization of monomer solutions require crosslinking to form the three dimensional network to gel the aqueous solution. HEMA monomer solutions typically can be crosslinked to gel by dimethacrylate, although other crosslinking agents, such as ethylene glycol dimethacrylate or methylmethacrylate, can also be used during polymerization to modify the hydrogel. A wide variety of other hydrophilic monomers may also be suitable.

Inorganic gels from which the hydrogel can be selected include, by way of example and not by way of limitation, silica, alumina, and ferric oxide. In addition, an adhesive can be introduced via a catheter to initially help seal the neck of an aneurysm, and can be selected from the group consisting of cyanoacrylates, gelatin/resorcinol/formol, mussel adhesive protein and autologous fibrinogen adhesive. It should thus be apparent that the hydrogel of the invention can be of a type that dissolves over time or one that remains as a permanent occlusive agent within the aneurysm. A radiopaque material may be incorporated into the hydrogel as fine particles of a selected radiopaque metal, such as gold or platinum.

A stretch resistant member 18 extends through the lumen of the vasoocclusive coil, and has a first or distal end 20 and a second or proximal end 22, with the first or distal end of the stretch resistant member fixedly attached to the vasoocclusive coil. The stretch resistant member and/or coil is detachably mounted at the second or proximal end to an elongated pusher member 24, to allow for placement of the vasoocclusive coil within the patient's vasculature. The stretch resistant member may be formed as a ribbon, wire, braid, primary wind, or stranded material, and may be formed from fiber, plastic or other polymer such as an ethylene-octene copolymer, polypropylene, or polyethylene, or a metal or metal alloy, which may be a radiopaque metal, such as platinum, for example. When the stretch resistant member is formed from a fiber such as an ethylene-octene copolymer, polypropylene, or polyethylene, a portion at or adjacent to the distal end of the coil may be attached to one end of the stretch resistant member by an adhesive such as a cyanoacrylate or by heating of the end of the fiber. The fiber may also be made to be radiopaque by forming the composition of the fiber to include a radiopaque material, such as powdered tantalum, tungsten, bismuth oxide or barium sulfate, for example.

As is illustrated in FIGS. 2 and 3, the stretch resistant member may be doubled and attached at its distal end 27 toward or at the distal end of the coil, forming a loop 28, having a proximal end 29. Referring to FIG. 1, a loop 30 formed of fiber material, metal or metal alloy, as described above, may be attached to the stretch resistant member, such as by an adhesive such as cyanoacrylate adhesive, for example. The loops 28 or 30 are typically connected to a connector fiber attached to the elongated pusher member, to detachably connect the stretch resistant member to the elongated pusher member, as will be further explained below. The coil itself may be detachably mounted to the distal end of the pusher member, for example, by one or more loops, such as a loop of fiber material 31 attached to the coil by an adhesive such as cyanoacrylate adhesive, for example, as is illustrated in FIG. 1, or by a loop 34 attached at the proximal end of the coil as a socket as shown in FIG. 2, or by a displaced end segment of the coil 36 at the proximal end of the coil as is illustrated in FIG. 3. As is shown in FIGS. 4 and 5, the proximal portion 37 of the stretch resistant member may also be bonded to the pusher member, such as by adhesive or by heat bonding. Connecting both the coil and stretch resistant member to the pusher member prevents the coil from sliding over the stretch resistant member to expose a kink point. In another alternate embodiment illustrated in FIG. 10, which is a variation of the embodiment of FIG. 3 in which the coil may be detachably mounted to the distal end of the pusher member by a displaced end segment of the coil 36 at the proximal end of the coil, the stretch resistant member may be doubled and attached at its distal end 27 toward the distal end of the coil, forming a loop 28, having a proximal end 29 which is looped around the displaced end segment of the coil.

The present invention also provides for an apparatus for release and deployment of the stretch resistant therapeutic device, such as the stretch resistant vasoocclusive coil 10, within a patient's vasculature. Means 38 are provided for detachably mounting the stretch resistant member from the distal end of the elongated pusher member. As is illustrated in FIGS. 1-3, in one aspect, a connector fiber 40 may be attached to the elongated pusher member, such as by an adhesive such as a cyanoacrylate adhesive, for example, or the connector fiber may be tied to the elongated pusher member, to detachably mount the vasoocclusive coil to the pusher member for placement of the vasoocclusive coil within the vasculature, and means 42 are provided for severing the connector fiber disposed adjacent to the connector fiber to cause the connector fiber to break and release the vasoocclusive coil for detaching and deploying the vasoocclusive coil from the pusher member when a desired placement of the vasoocclusive coil within the vasculature is achieved. The means for severing the connector fiber may include an electrical resistance heater wire or coil 44 connected via electrical line 46 to a control unit 48, for example, when the connector fiber is formed from a thermoplastic material, such as polyethylene, for example.

Referring to FIGS. 4 and 5, another embodiment of the invention provides for a stretch resistant therapeutic device such as a vasoocclusive coil 10 with a proximal end 12, a distal end 14, a lumen 16 extending between the proximal and distal ends, and the stretch resistant member 18 extending through the lumen of the vasoocclusive coil, with a first or distal end 20 of the stretch resistant member fixedly attached to the therapeutic device and the second or proximal end 22 of the stretch resistant member fixedly attached to the elongated pusher member 24. As noted above, the stretch resistant member may be formed as a ribbon, wire, braid, primary wind, or stranded material, and may be formed from fiber, plastic or other polymer such as an ethylene-octene copolymer, polypropylene, or polyethylene, or a metal such as platinum, for example. The stretch resistant member may be bonded to the pusher member by an adhesive such as a cyanoacrylate adhesive, for example, but when the stretch resistant member is formed from a fiber such as an ethylene-octene copolymer, polypropylene, or polyethylene, the second or proximal end of the stretch resistant member may be attached the pusher member by an adhesive such as a cyanoacrylate or by heating of the second or proximal end of the fiber. A connector fiber 40, such as a polyethylene fiber, may be attached to an outer portion of the elongated pusher member as shown in FIGS. 4 and 5, by an adhesive such as a cyanoacrylate adhesive, for example, or by heat bonding, or the connector fiber may be tied to the elongated pusher member, to detachably mount the therapeutic device to the pusher member, such as by the loop 34 attached to the coil or a displaced end segment of the coil, for placement of the therapeutic device within the vasculature. As noted above, means 42 for severing the connector fiber may include an electrical resistance heater wire or coil 44 connected via electrical line 46 to a control unit 48, for example.

Figure 7:
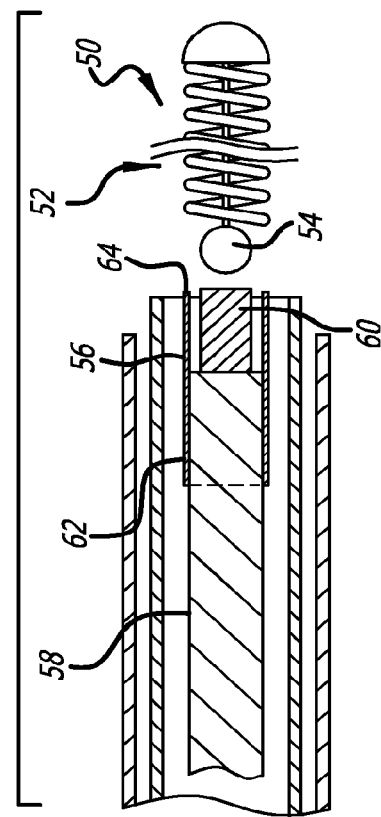
FIG. 7 is a sectional view of the stretch resistant therapeutic device and an apparatus for release and deployment of the stretch resistant therapeutic device of FIG. 6, showing release of the stretch resistant therapeutic device.

In another embodiment illustrated in FIGS. 6 and 7, in which the therapeutic device may be released mechanically, the proximal end of the therapeutic device includes a distal therapeutic portion 50 and a proximal stem portion 52, and the proximal stem portion including at least one rounded member 54. A body of constraining material 56 is mounted to the distal end of an elongated pusher member 58, with the body of constraining material having a stressed configuration engaging the rounded member of the stem proximal portion of the vasoocclusive coil, as is shown in FIG. 6, and a recovered configuration withdrawn from the rounded member of the proximal stem portion of the therapeutic device, as is shown in FIG. 7. An end portion 60 at the distal end of the elongated pusher member may contact the rounded member of the proximal stem portion of the therapeutic device. In one option, the body of constraining material may have a tubular cross-section forming a tubular collar extending from its proximal end 62 to its distal end 64 and the end portion is located internally to the tubular collar for engaging the rounded member of the proximal stem portion of the therapeutic device upon shape recovery of the tubular collar to dislodge the therapeutic device from the tubular collar. The body of constraining material may be formed of a polymer such as polyurethane, or a nickel titanium alloy, for example.

Alternatively, the therapeutic device may be released by injection, as is illustrated in FIGS. 8 and 9. Referring to FIG. 8, the proximal end of the therapeutic device includes a distal therapeutic portion 50 and a proximal stem portion 52, and the proximal stem portion including at least one rounded member 54. A therapeutic device delivery assembly 70 is provided, including an elongated flexible tubular catheter 72 having a distal end 74. The flexible tubular catheter 72 can be formed, for example, from polyethylene, polyethylene terephthalate, polyvinyl chloride, nylon and ionomers, or other similar suitable polymers, stainless steel or nickel titanium alloy hypo tubes, and the like. In one embodiment, the distal end of the elongated flexible tubular catheter has a frustoconical shape. The flexible tubular catheter 72 may include a tubular distal tip 76 having a proximal end 78 mounted to the outer surface of the distal end of the flexible tubular catheter, such as by adhesive bonding, such as with a cyanoacrylate adhesive, for example. The tubular distal tip may alternatively be heat bonded to the distal end of the flexible tubular catheter, or may be mounted to the distal end of the flexible tubular catheter by other suitable means. The tubular distal tip has an inner lumen 80, and a distal end 82 with a surface defining a distal opening 84. In one aspect, the diameter of the distal end of the tubular distal tip is smaller than the proximal end, allowing the proximal end of the therapeutic device to be captured within the inner lumen of the tubular distal tip. The tubular distal tip thus has a generally frustoconical shape. Alternatively, a cylindrical tubular shape for the distal end of the catheter and the tubular distal tip may also be suitable.

The tubular distal tip is typically formed of a yieldable material that is sufficiently rigid to retain the proximal end of the therapeutic device within the inner lumen of the tubular distal tip. The yieldable material can be, for example, a shape memory polymer, an elastomer such as polyurethane, nylon, PEBAX polymer, Teloflex, polybutyl terephthalate (PBT), polymers available under the trade names PEBAX, Hytrel, Arnitel, Riteflex, heat shrink tubing such as polyethylene terephthalate (PET) or high density polyethylene (HDPE), or a shape memory metal such as nickel titanium alloy, such as that available under the trade name NITINOL.

Means are also provided for dislodging the proximal end of the therapeutic device captured in the inner lumen of the tubular distal tip to expel the proximal end of the therapeutic device from the distal opening of the tubular distal tip at the desired location for treatment within the vasculature of a patient. As is illustrated in FIG. 8, the means for dislodging the proximal end of the therapeutic device from the inner lumen of the tubular distal tip may be an elongated flexible pusher member 86, such as a flexible metal wire coaxially disposed within the elongated flexible tubular catheter. The proximal end 88 of the pusher member extends from the proximal end of the elongated flexible tubular catheter, and may include a flange or stop portion 90 at the proximal end of the pusher member for limiting the movement of the pusher member through the delivery catheter, and the distal end 92 of the pusher member is adapted to contact and dislodge the proximal end of the therapeutic device from the tubular distal tip. The distal end of the pusher member may also have a corresponding frustoconical shape, so as to be extendable to the distal end of the catheter to force the proximal end of the therapeutic device from the yieldable tubular distal tip to dislodge the proximal end of the therapeutic device.

An hydraulic release mechanism, may also be used for injecting the therapeutic device. As is illustrated in FIG. 9, the tubular distal tip may be dimensioned so as to form a tight fluid seal about the proximal end of the endoluminal device, and the means for dislodging the endoluminal device may be a syringe 94 having a plunger 96 for pressurizing a fluid, such as saline solution, for example, in a fluid chamber 98 to supply pressurized fluid through a flexible nozzle 100 that can be connected to the proximal end of the elongated flexible tubular catheter for supplying the pressurized fluid within the elongated flexible tubular catheter to expel the proximal end of the endoluminal device from the tubular distal tip.

It should be recognized that other mechanisms for releasing the stretch resistant therapeutic devices may also be utilized, such as a rotational release mechanism, for example. It will be apparent from the foregoing that while particular forms of the invention have been illustrated and described, various modifications can be made without departing from the spirit and scope of the invention. Accordingly, it is not intended that the invention be limited, except as by the appended claims.

We claim:

1. An apparatus for release and deployment of a stretch resistant therapeutic device within a patient's vasculature, comprising:
    a vasoocclusive coil having a proximal end and a distal end, said vasoocclusive coil defining a lumen between said proximal and distal ends, said vasoocclusive coil including a distal therapeutic portion and a proximal stem portion, said proximal stem portion including at least one rounded member;
    an elongated pusher member having a distal end adjacent to said proximal end of said vasoocclusive coil;
    a stretch resistant member extending through said lumen of said vasoocclusive coil, said stretch resistant member being fixedly attached to said vasoocclusive coil at the distal end of the vasoocclusive coil and detachably mounted to the distal end of the elongated pusher member to allow for placement of the vasoocclusive coil within the patient's vasculature; and
    a body of constraining material having a tubular cross-section forming a tubular collar mounted to the distal end of the elongated pusher member detachably retaining said at least one rounded member, said body of constraining material having a stressed configuration engaging said at least one rounded member of the stem proximal portion of the vasoocclusive coil and a recovered configuration withdrawn from said at least one rounded member of the proximal stem portion of the vasoocclusive coil, said distal end of said elongated pusher member contacting said at least one rounded member when said body of constraining material changes from said stressed configuration to said recovered configuration withdrawn from said at least one rounded member of the proximal stem portion of the vasoocclusive coil to dislodge said at least one rounded member from said body of constraining material to release said vasoocclusive coil from said elongated pusher member.

2. The apparatus of claim 1, wherein said body of constraining material is axially stressed in said stressed configuration to engage said proximal stem portion of the vasoocclusive coil.

3. The apparatus of claim 2, wherein said body of constraining material has a tubular cross-section forming a tubular collar extending from its proximal end to its distal end and said end portion is located internally to said tubular collar for, upon shape recovery of said tubular collar, engaging said vasoocclusive coil to dislodge said vasoocclusive coil from said tubular collar.

4. The apparatus of claim 1, wherein said body of constraining material is comprised of a polymer.

5. The apparatus of claim 1, wherein said body of constraining material is comprised of polyurethane.

6. The apparatus of claim 1, wherein said body of constraining material is comprised of a nickel titanium alloy.

7. The apparatus of claim 1, wherein said stretch resistant member is radiopaque.

8. The apparatus of claim 1, wherein said stretch resistant member is formed of a stranded material.

9. The apparatus of claim 1, wherein said stretch resistant member is a fiber formed from a polymer.

10. The apparatus of claim 9, wherein the stretch resistant member has first and second ends, and the vasoocclusive coil is attached to the first end of the stretch resistant member by heating of the end of the fiber.

11. The apparatus of claim 1, wherein said stretch resistant member is a fiber formed from a polymer selected from the group consisting of an ethylene-octene copolymer, polypropylene, and polyethylene.

12. The apparatus of claim 11, wherein the stretch resistant member has first and second ends, and the vasoocclusive coil is attached to the first end of the stretch resistant member by heating of the end of the fiber.

* * * * *